US010238364B2

(12) United States Patent
Deladi et al.

(10) Patent No.: US 10,238,364 B2
(45) Date of Patent: Mar. 26, 2019

(54) MEDICAL DEVICE WITH ULTRASOUND TRANSDUCERS EMBEDDED IN FLEXIBLE FOIL

(75) Inventors: Szabolcs Deladi, Eindhoven (NL); Cornelius Antonius Nicolaas Maria Van Der Vleuten, Eindhoven (NL); Antonius Johannes Josephus Rademakers, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 385 days.

(21) Appl. No.: 13/885,796

(22) PCT Filed: Oct. 3, 2011

(86) PCT No.: PCT/IB2011/054330
§ 371 (c)(1),
(2), (4) Date: Feb. 4, 2014

(87) PCT Pub. No.: WO2012/066430
PCT Pub. Date: May 24, 2012

(65) Prior Publication Data
US 2014/0148703 A1 May 29, 2014

(30) Foreign Application Priority Data
Nov. 18, 2010 (EP) .................................. 10191687

(51) Int. Cl.
*A61B 8/00* (2006.01)
*A61B 8/08* (2006.01)
*A61B 8/12* (2006.01)
*B06B 1/06* (2006.01)
*A61B 34/20* (2016.01)
(Continued)

(52) U.S. Cl.
CPC .......... *A61B 8/4483* (2013.01); *A61B 8/0883* (2013.01); *A61B 8/12* (2013.01); *A61B 8/445* (2013.01); *A61B 34/20* (2016.02); *B06B 1/0629* (2013.01); *A61B 18/1492* (2013.01); *A61B 2018/00738* (2013.01); *A61B 2018/00839* (2013.01); *A61B 2034/2051* (2016.02); *A61B 2034/2063* (2016.02);
(Continued)

(58) Field of Classification Search
None
See application file for complete search history.

(56) References Cited

U.S. PATENT DOCUMENTS

| 5,515,853 A | 5/1996 | Smith et al. |
| 5,655,276 A | 8/1997 | Pattanayak et al. |

(Continued)

FOREIGN PATENT DOCUMENTS

| CN | 1168625 A | 12/1997 |
| CN | 101405090 A | 4/2009 |

(Continued)

*Primary Examiner* — Patricia J Park
*Assistant Examiner* — Nate Sunwoo

(57) ABSTRACT

The invention relates to ultrasound imaging method and apparatus suitable for minimally invasive ultrasound diagnostic devices in cardiac ablation monitoring and in tumor ablation monitoring. The present invention proposes to manufacture a transducers assembly and system on a patterned flexible foil by embedding transducers patches in apertures on the foil surface. This provides great control of the acoustic properties of the transducer.

13 Claims, 6 Drawing Sheets

(51) Int. Cl.
*A61B 18/14* (2006.01)
*A61B 18/00* (2006.01)
*G01S 15/46* (2006.01)
*A61B 90/00* (2016.01)

(52) U.S. Cl.
CPC . *A61B 2090/364* (2016.02); *A61B 2090/3782* (2016.02); *G01S 2015/465* (2013.01); *Y10T 29/42* (2015.01)

(56) References Cited

U.S. PATENT DOCUMENTS

| | | | |
|---|---|---|---|
| 5,684,884 | A | 11/1997 | Nakaya et al. |
| 6,298,261 | B1 | 10/2001 | Rex |
| 6,311,000 | B1 * | 10/2001 | Schneider ............ G02B 6/4432 |
| | | | 385/106 |
| 6,476,541 | B1 * | 11/2002 | Smith .................. A61B 5/0097 |
| | | | 310/334 |
| 6,788,967 | B2 | 9/2004 | Ben-Haim et al. |
| 6,806,622 | B1 * | 10/2004 | Schmidt .................. B06B 1/067 |
| | | | 310/327 |
| 6,896,657 | B2 | 5/2005 | Willis |
| 7,573,181 | B2 | 8/2009 | Rhim et al. |
| 7,575,550 | B1 | 8/2009 | Govari |
| 7,604,601 | B2 | 10/2009 | Altmann et al. |
| 7,834,522 | B2 | 11/2010 | Guo |
| 7,846,101 | B2 | 12/2010 | Eberle et al. |
| 8,475,524 | B2 | 7/2013 | Schwartz |
| 9,901,321 | B2 | 2/2018 | Harks et al. |
| 2002/0107445 | A1 | 8/2002 | Govari |
| 2002/0153805 | A1 * | 10/2002 | Smith .................. A61B 5/0097 |
| | | | 310/311 |
| 2003/0093067 | A1 | 5/2003 | Panescu |
| 2004/0049121 | A1 | 3/2004 | Yaron |
| 2004/0054289 | A1 | 3/2004 | Eberle et al. |
| 2004/0215079 | A1 * | 10/2004 | Omura ............... G01N 29/2456 |
| | | | 600/459 |
| 2005/0156491 | A1 * | 7/2005 | Scott ...................... B06B 1/064 |
| | | | 310/334 |
| 2006/0253032 | A1 | 11/2006 | Altmann et al. |
| 2007/0027392 | A1 | 2/2007 | Schwartz |
| 2007/0049821 | A1 | 3/2007 | Willis |
| 2007/0106147 | A1 * | 5/2007 | Altmann .................. A61B 8/12 |
| | | | 600/407 |
| 2008/0125658 | A1 | 3/2008 | Lee et al. |
| 2009/0015109 | A1 * | 1/2009 | Schuh ................ H01L 41/0471 |
| | | | 310/364 |
| 2009/0034370 | A1 * | 2/2009 | Guo ..................... B06B 1/0622 |
| | | | 367/180 |
| 2009/0264767 | A1 * | 10/2009 | Griffin ..................... A61B 8/12 |
| | | | 600/459 |
| 2012/0004547 | A1 | 1/2012 | Harks et al. |
| 2014/0148703 | A1 | 5/2014 | Deladi et al. |

FOREIGN PATENT DOCUMENTS

| | | | |
|---|---|---|---|
| EP | 0685985 | 5/1995 | |
| EP | 0685985 A2 * | 12/1995 | ............ H04R 17/00 |
| EP | 1362553 A1 | 11/2003 | |
| JP | 2001299756 A | 10/2001 | |
| JP | 2006025960 A | 2/2006 | |
| JP | 2006280591 A | 10/2006 | |
| JP | 2008079909 | 4/2008 | |

* cited by examiner

MEDICAL DEVICE WITH ULTRASOUND TRANSDUCERS EMBEDDED IN FLEXIBLE FOIL

FIELD OF THE INVENTION

The invention relates to ultrasound imaging apparatus suitable for minimally invasive ultrasound diagnostic devices. The invention can be used for fabrication of interventional devices used in cardiac ablation monitoring and in cancer ablation monitoring.

BACKGROUND OF THE INVENTION

Radio frequency (RF) catheter ablation is an invasive procedure used to remove faulty electrical pathways from patients who are prone to develop cardiac arrhythmias such as atrial fibrillation (AF). In AF ablation procedures, complete electrical isolation of the pulmonary veins is targeted and this is achieved by creating lesion lines with an ablation catheter.

The majority of the catheter ablation procedures are performed with "single-point ablation catheters". Lesion lines can be created with such catheters by sequential point by point ablation. To achieve complete electrical isolation of the pulmonary veins lesion lines are created meeting the two requirements of being transmural and continuous.

A requirement for RF catheters is a more adequate control. A system that can provide a real-time feedback of the lesion development in the tissue, and can provide real-time information about the depth of the lesion with respect to the thickness of the tissue at the treatment site, would prevent injury and potential death from overheating in (RF) catheter ablation procedures, while insufficient heating results in recurrence of arrythmia. It has been shown that high-frequency ultrasound can be used to monitor the progression of the lesion boundary in M-mode imaging.

Embedding ultrasound transducers in ablation catheters enables real-time feedback on lesion front progression.

U.S. Pat. No. 7,846,101 discloses an intravascular ultrasound imaging apparatus comprising a transducer assembly. The assembly includes a flexible circuit comprising transducer elements attached to a flexible substrate. However, as the flexible substrate is part of the material stack forming the assembly, the flexible foil may produce acoustical effect adverse to the transducer elements performance.

The inventor of the present invention has appreciated that an improved transducer assembly is of benefit, and has in consequence devised the present invention. In particular it would be advantageous to realize a transducer assembly having acoustic properties depending only on the transducer element material. It would also be desirable to enable the user of RF catheter to access real-time feedback of the lesion development in tissue during RF catheter ablation procedure.

SUMMARY OF THE INVENTION

In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention an ultrasound transducer assembly is presented that comprises a flexible foil having openings extending from a top to a bottom surface of the flexible foil; one or more piezoelectric elements contained into the openings and fastened to the internal rim of the openings; one or more conductive layers deposited on the flexible foil and on the one or more piezoelectric elements.

By placing piezoelectric elements into the openings of the flexible foil, the properties of piezoelectric elements are not influenced by the material of the flexible foil and therefore desired tuning of the performance of the transducer assembly can be obtained. As the transducer assembly comprises one or more piezoelectric elements embedded into the flexible foil, the flexible foil does not influence the acoustical performance of the transducer. The inside edge, i.e. the internal rim of the opening of the flexible foil is fastened to the piezoelectric element, i.e. the external edge of the piezoelectric element.

The flexible foil maybe e.g. a Kapton foil, metalized with, e.g. copper, having openings, i.e. holes to contain piezoelectric elements. The piezoelectric elements are, e.g. piezoelectric patches.

In some embodiments the flexible foil comprises metallization tracks.

In some embodiments the one or more conductive layers is/are deposited on the top and the bottom surface of the flexible foil and on the top and the bottom surface of the one or more piezoelectric elements.

In some other embodiments the one or more conductive layers are two layers, the first layer deposited on the top surface of the flexible foil and on the top of the one or more piezoelectric elements and the second layer deposited on the bottom surface of the flexible foil and on the bottom surface of the one or more piezoelectric elements. Through the deposition of these conductive layers, the assembly is provided with a top electrode on the piezoelectric elements, which is connected to the top metallization layer of the flexible foil and a bottom electrode on the piezoelectric element which is connected to the bottom metallization layer of the flexible foil.

In some other embodiments the one or more conductive layers is one layer deposited on the bottom surface of the flexible foil and on the bottom surface of the one or more piezoelectric elements. This provides great advantages for protection of the electrical signal of the transducer from adverse external perturbations and is useful in the realization of the Faraday cage around the bottom electrode avoiding RF signal interference with ultrasound signal during ablation.

In a second aspect of the invention an ultrasound transducer system is presented that comprises: an ultrasound transducer assembly according to the first aspect of the invention placed in a base structure; the base structure comprising cavities, wherein the cavities are filled with backing material; a coating layer deposited on the external surface of the ultrasound transducer assembly.

In some embodiments at least one of the cavities of the ultrasound transducer system extends from the top to the bottom surface of the base structure. The cavities of the base structure may be considered as apertures in the base structure, providing access to the back side or back surface of the piezoelectric element placed on the base structure. The cavities in the base structure may communicate with each other, e.g. in presence of multiple piezoelectric elements or can be accessed individually.

The ultrasound transducer assembly placed on the base structure may be glued on and around the base structure. When the ultrasound transducer assembly is placed on the base structure, the empty cavities located at the backside, i.e.

at the bottom surface, of the transducer elements are filled with backing material. In this way the performance of the transducer are only dependent on the piezoelectric and the backing materials, and are not influenced by the flexible foil. The flexible foil is not supporting the piezoelectric elements and the piezoelectric elements are embedded into it.

In placing the ultrasound transducer assembly onto the base structure, the openings of the flexible foil in which the piezoelectric elements are fasten, e.g. by means of glue, are located in positions corresponding to the cavities of the base structure. The back side or bottom surface of the piezoelectric elements is therefore accessible though the cavities of the base structure. The modality of addition of the backing material allows for freedom and good control of the appropriate choice of the material. For example, the filling material can be dispensed into the cavities by injection in a fluidic state through conducts in the base structure. Examples of filling materials comprises adhesive which can rapidly bond to plastics and metal upon exposure to UV and/or visible light. Filling materials compositions may also comprise microspheres, such as ceramic or glass sphere, which can be hollow, lightweight and with a high compressive strength.

In some other embodiments of the ultrasound transducer assembly according to the first aspect of the invention, the fastening comprises at least a side wall of one or more piezoelectric elements glued to the internal rim of the openings. By gluing only the side or later wall of the piezoelectric elements the piezoelectric elements the acoustic properties of the piezoelectric system are not influenced by the flexible foil.

The invention is of great advantage in particular in the fabrication of high frequency (HF) transducers. In traditional HF transducers, the flexible foil is included in the transducer stack and the transducer elements are place onto the flexible foil. As the higher the frequency, the lower the thickness of the piezoelectric elements, traditional HF transducers have a high chance of failure due to high risk of breakdown as the electrodes from the front side and the backside of the piezoelectric material are becoming too close with respect to each other. The invention, by embedding the piezoelectric elements into the flexible foil, provides a solution which is therefore particularly advantageous for HF transducers.

In some embodiments the one or more piezoelectric elements is/are glued with non-conductive glue.

In some embodiments the one or more piezoelectric elements is/are fastened to the internal rim of the openings by an isolation layer, i.e. a layer having isolating properties.

In some other embodiments the ultrasound transducer assembly according to the first aspect of the invention further comprises an isolation layer deposited onto the external surface of the ultrasound transducer assembly. This electrical isolation layer may be a matching layer coating the ultrasound transducer assembly for maximizing the acoustic performance of the transducer elements.

In a third aspect of the invention a catheter tip is presented that comprises an ultrasound transducer assembly according to the first aspect of the invention.

In a fourth aspect of the invention a catheter tip is presented that comprises an ultrasound transducer system according to the second aspect of the invention.

The catheter tip may have irrigation holes through which the ultrasound transducer system communicates externally towards the environment, e.g. a pulmonary vein.

The catheter tip may also have other openings through which the ultrasound transducers system can follow the ablation procedure of tissue unobstructed, e. g. for optical fibers. Alternatively, in case an ultrasound transparent medium is used for ablation e.g. polymethylpentene coated with a thin platinum layer then the tip should not necessarily contain openings.

When the ultrasound transducers is embedded in ablation catheters for enable real-time feedback on lesion front progression, the ablation cap can be mounted on the catheter body after the ultrasound transducers system is electrically connected and fixed in the catheter tip.

In a fifth aspect of the invention a method for fabricating an ultrasound transducer assembly is presented that comprises: providing a flexible foil having openings extending from the top to the bottom surface of the flexible foil; mounting one or more piezoelectric elements into the openings; depositing one or more conductive layers on the flexible foil and the one or more piezoelectric elements.

In some embodiments according to the fifth aspect of the invention the mounting comprises inserting the one or more piezoelectric elements into the openings and gluing said one or more piezoelectric elements to the internal rim of the openings.

In some embodiments according to the fifth aspect of the invention the depositing comprises depositing one or more conductive layers on the top and bottom surface of the flexible foil and on the top and the bottom surface of the one or more piezoelectric elements.

In a sixth aspect of the invention a method for fabricating an ultrasound transducer system is presented that comprises: positioning the ultrasound transducer assembly according to the first aspect of the invention onto a base structure, the base structure comprising cavities; filling the cavities with backing material; depositing a coating layer on the external surface of the ultrasound transducer assembly.

In some embodiments according to this last aspect the positioning comprises folding into a 3D structure the flexible foil containing the one or more piezoelectric elements and gluing the folded flexible foil around the base structure.

In some embodiments according to this last aspect the filling comprises dispensing backing material in a fluidic state and hardening the backing material. In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings.

DESCRIPTION OF EMBODIMENTS

Figure 1:
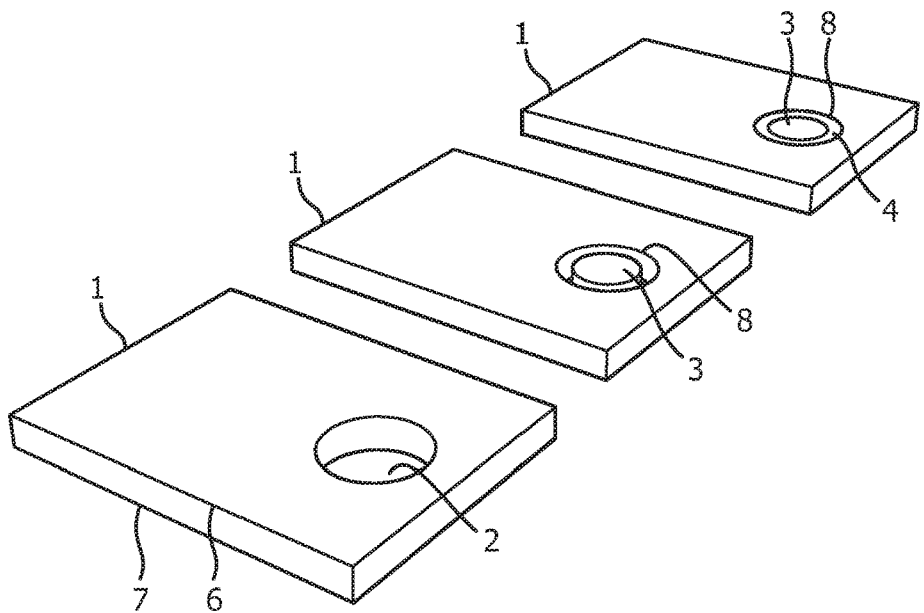
FIG. 1 shows a perspective view of a flexible foil with patterned openings according to embodiments of the invention.

FIG. 1 shows three steps of the method for fabricating an ultrasound transducer according to one aspect of the invention. On the flexible foil 1 a desired patterned is produced, e.g. opening 2, extending from the top surface 6 to a bottom surface 7. Piezoelectric elements, e.g. piezoelectric element 3, are located in into the openings, e.g. opening 2 and fastened to the internal rim 8 of opening 2. Non-conductive glue 4 may be used to fasten the piezoelectric element 3 to the internal rim 8 of opening 2.

Figure 2A:
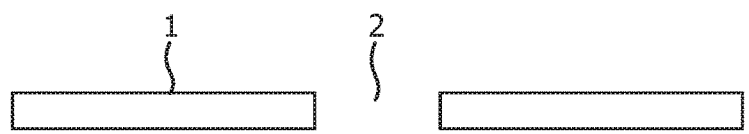
FIG. 2a shows a cross section of the flexible foil as shown in FIG. 1.
Figure 2B:
FIG. 2b shows a cross section of the flexible foil including a piezoelectric element according to embodiments of the invention.

FIG. 2a shows a cross section of the flexible foil 1 before including the piezoelectric elements. The opening 2 is filled, as shown in FIG. 2b by a piezoelectric element 3. The mounting of the piezoelectric element 3, e.g. a piezoelectric patch, is achieved by gluing the patches in the designated areas at the rim or edge of the opening 2. In some embodiments the mounting of the piezoelectric element 3 may be achieved by gluing a thin peripheral annular region of the piezoelectric patch 3 on the flexible foil 1.

FIG. 2b shows the flexible foil 1 with opening 2 where the piezoelectric element 3 is located into the opening 2.

Figure 2C:
FIG. 2c shows a cross section of the flexible foil including a piezoelectric element glued into the opening of the flexible foil according to embodiments of the invention.

FIG. 2c shows the transducer assembly of FIG. 2b where the piezoelectric element 3, i.e. the external edge of the piezoelectric element 3, is fastened to the inside edge, i.e. the internal rim of the opening 2 of the flexible foil 1 by means of glue 4. The glue may be non-conductive glue so as to provide isolation of the piezoelectric element 3, e.g. piezoelectric patch from the flexible foil 1.

Figure 3A:
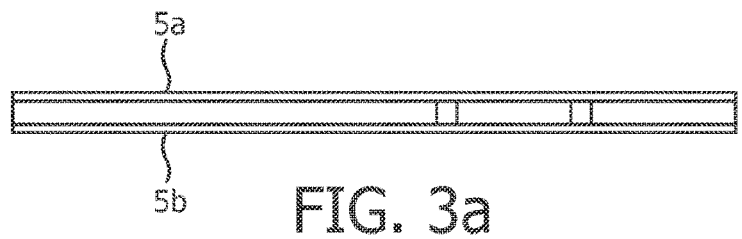
FIG. 3a shows a cross section of the flexible foil as shown in FIG. 2c where conducting electrodes are deposited.

FIG. 3a shows the transducer assembly of FIG. 2c after conductive layers 5 are deposited on the flexible foil 1 and on the piezoelectric element 2. In particular conductive layer 5a is deposited on the top surface of the flexible foil 1 and of the piezoelectric element 2 providing the top electrode, while the conductive layer 5b is deposited on the bottom surface of the flexible foil 1 and of the piezoelectric element 2 providing the bottom electrode.

Figure 3B:
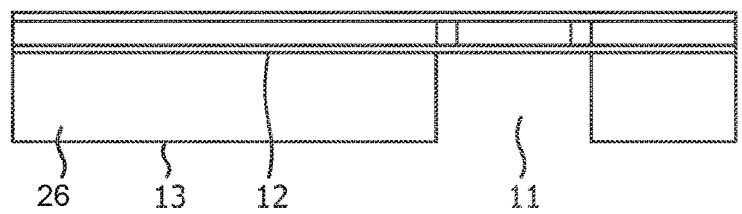
FIG. 3b shows a cross section of the flexible foil as shown in FIG. 3a positioned on a base or supporting structure.
Figure 3C:
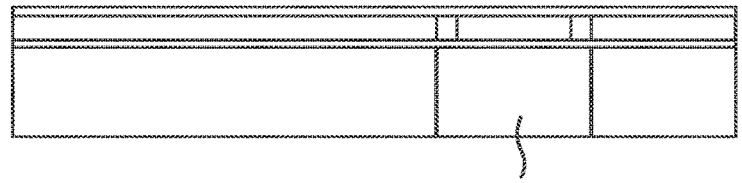
FIG. 3c shows a cross section of the transducer assembly as shown in FIG. 3b where the cavities in the base structure are filled with backing material.

In FIG. 3b the transducer assembly of FIG. 3a is then placed onto a base structure 26, characterized by cavities 11 extending from the top surface 12 to the bottom surface 13 of the base structure 26. The transducer assembly is filled with backing material 7 as shown in FIG. 3c.

Figure 4A:
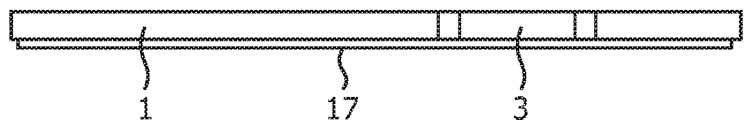
FIG. 4a shows a cross section of the flexible foil as shown in FIG. 2c where a single conducting electrode is deposited on the back surface of the flexible foil and piezoelectric element.
Figure 4B:
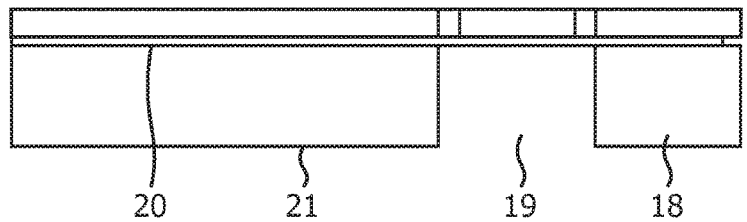
FIG. 4b shows a cross section of the flexible foil as shown in FIG. 4a positioned on a base or supporting structure.

In some other embodiments one layer is deposited on the bottom surface of the flexible foil and on the bottom surface of the one or more piezoelectric element. FIG. 4a shows a cross section of the flexible foil as shown in FIG. 2c where a single conducting layer 17 is deposited on the back surface of the flexible foil 1 and piezoelectric element 3. The transducer assembly of FIG. 4a is then placed onto a base structure 18, characterized by cavities 19 extending from the top surface 20 to the bottom surface 21 of the base structure 18 as shown in FIG. 4b.

Figure 4C:
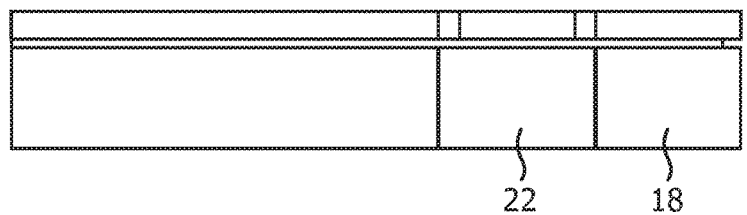
FIG. 4c shows a cross section of the transducer assembly as shown in FIG. 4b where the cavities in the base structure are filled with backing material.

The transducer assembly placed on the base structure 18 is filled with backing material 22 as shown in FIG. 4c.

Figure 4D:
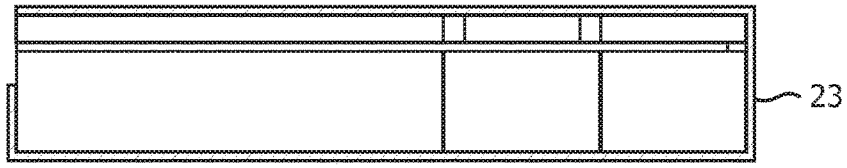
FIG. 4d shows a cross section of the transducer system as shown in FIG. 4c where a conducting electrode is deposited around the transducer system.
Figure 4E:
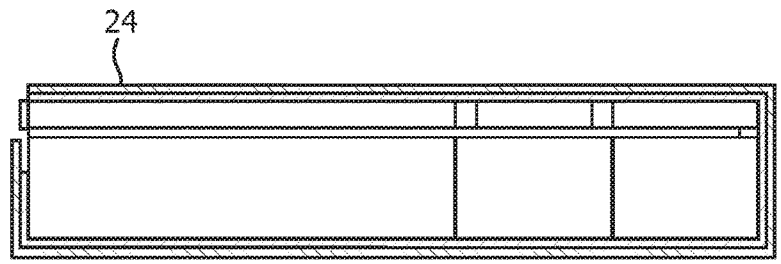
FIG. 4e shows a cross section of the transducer system as shown in FIG. 4d where a matching or electrical isolation layer is deposited around the transducer system.

In FIG. 4d a coating layer 23, which may be a conducting electrode, is deposited at least partially around the transducer system as shown in FIG. 4c. The transducer system as shown in FIG. 4d can be further coated by a matching or electrical isolation layer 24 deposited around the transducer system.

The embodiment shown in FIGS. 4a-4e is an alternative to the embodiments shown in FIGS. 3a-3c and provides great advantages for electrical signal isolation purposes.

Figure 5:
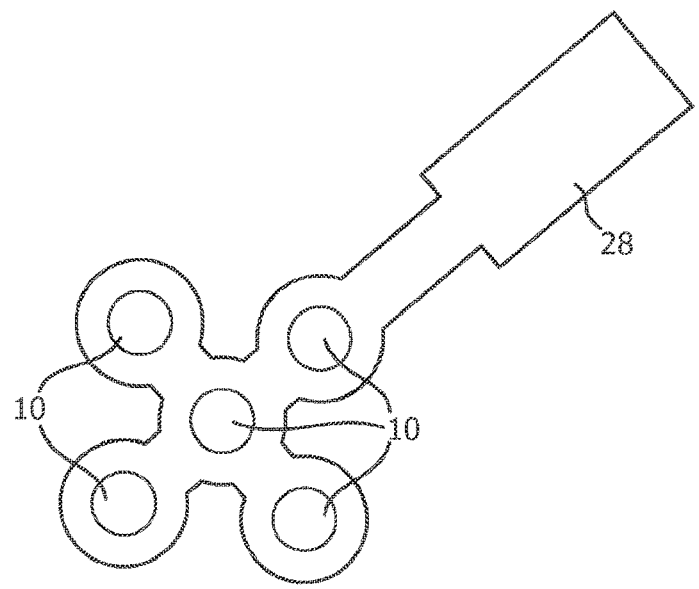
FIG. 5 shows a top view of a patterned flexible foil including transducer elements according to embodiments of the invention.
Figure 6:
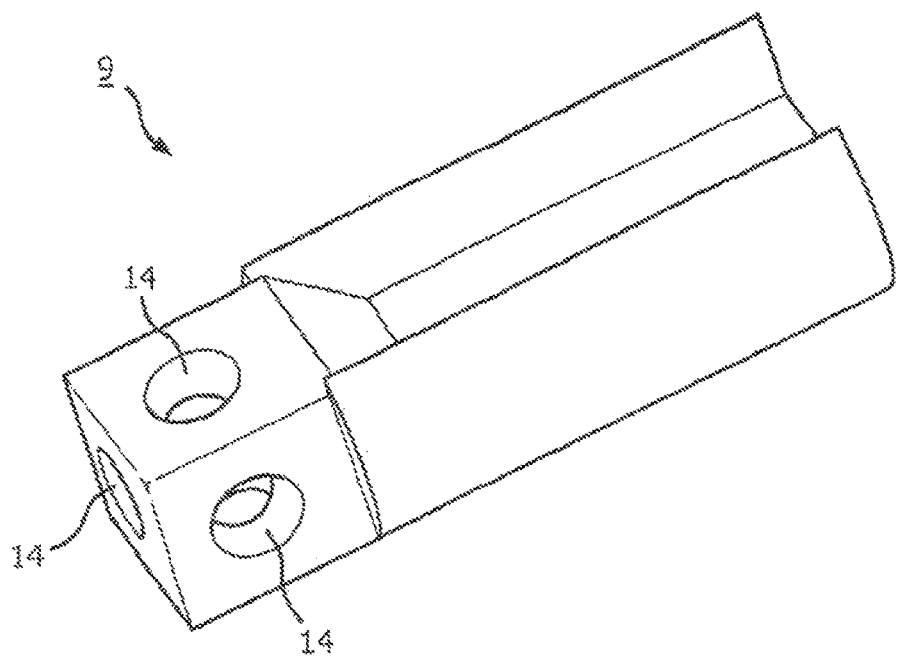
FIG. 6 shows a perspective view of a base element according to embodiments of the invention.
Figure 7:
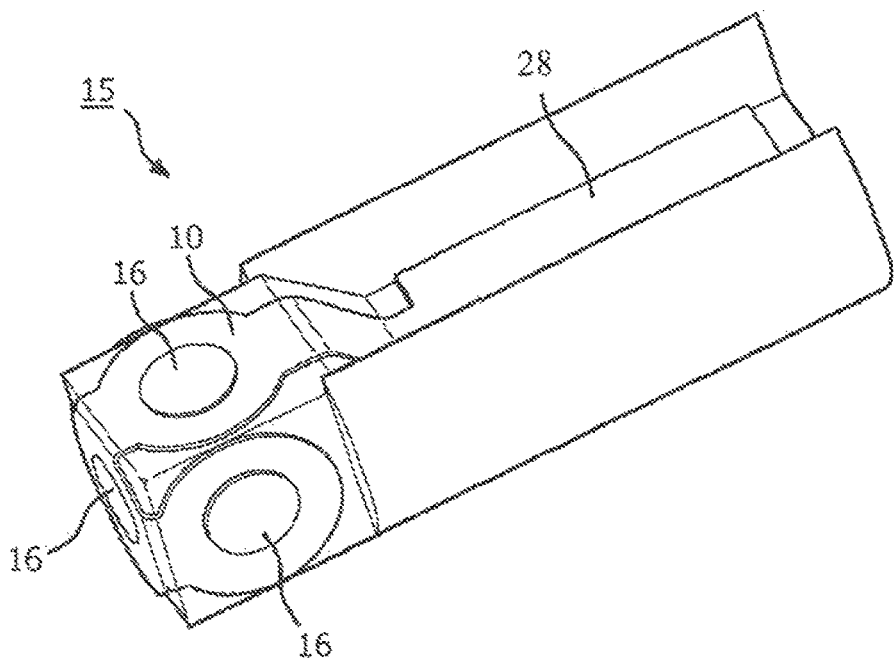
FIG. 7 shows an ultrasound transducer system according to embodiments of the invention.

FIG. 5 shows a top view of a patterned flexible foil including transducer elements according to an embodiment of the invention. The flexible foil 28 is patterned so as to have a cross-shape having five openings 10 in which piezoelectric elements 16 are going to be introduced. Shape and number of openings depend on the base structure to be used and on the number of piezoelectric elements to be fasten. This is within the knowledge of the person skilled in the art. The flexible foil 28 is designed so as to be folded in a three-dimensional structure with matches, e.g. in one embodiment the shape of the base structure 9 having cavities 14 as shown in FIG. 6. By folding and gluing the ultrasound transducer assembly onto the base structure the ultrasound transducer system 15 is produced as shown in FIG. 7. The piezoelectric elements 16 fastened into the openings 10 of the flexible foil 28 are positioned so as to face the cavities 14 of the base structure 9. The cavities 14 are then filled with backing materials. The filling may be achieved through injection of backing material in fluidic state followed by hardening. Hardening may be achieved e.g. by curing in air, through exposure to high temperature, exposure to UV light or through the use of chemicals, such as chemical catalyst. In case of hardening with UV exposure, the base structure 9 is made of UV transparent material.

A further coating layer is deposited on the external surface of the ultrasound transducer assembly 15 so as to provide electrical isolation from external disturbance, e.g. RF ablation.

Figure 9:
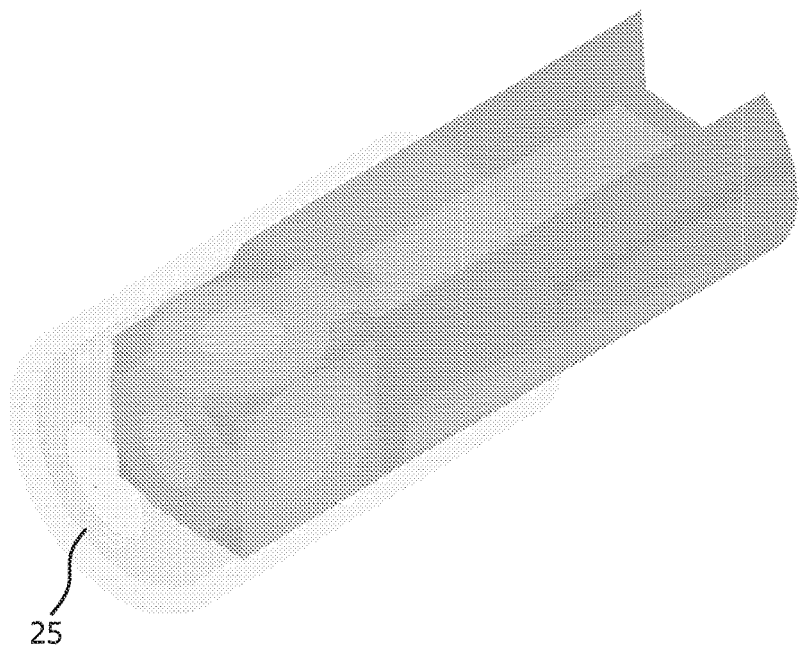
FIG. 9 shows a prospective view of an ultrasound transducer system according to embodiments of the invention comprising an ablation cap.
Figure 10:
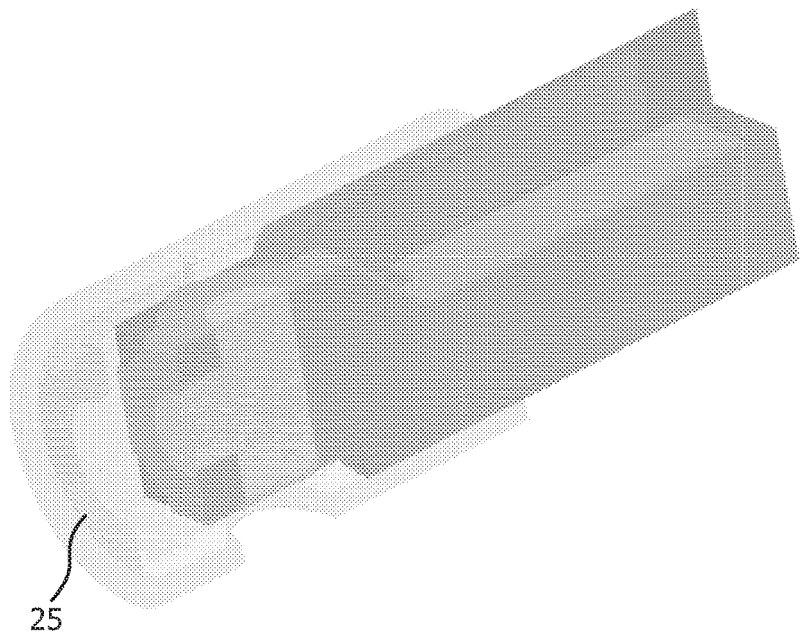
FIG. 10 shows a cross section view of an ultrasound transducer system according to embodiments of the invention comprising an ablation cap.

In cardiac ablation monitoring, the ultrasound transducer system can be connected and fixed in a catheter tip of a catheter allowing for forward and sideward monitoring during ablation. After the ultrasound transducer system is electrically connected and fixed in the catheter tip, the ablation cap, e.g. a platinum ablation cap 25 as shown in FIGS. 9 and 10, can be mounted on the catheter body. The ablation tip may have apertures though which the ultrasound transducer system can follow the ablation procedure. Alternatively a material, such as polymethylpentene coated with thin platinum layer, which is transparent to ultrasound may be used. This avoids the need of apertures in the ablation tip.

Figure 8:
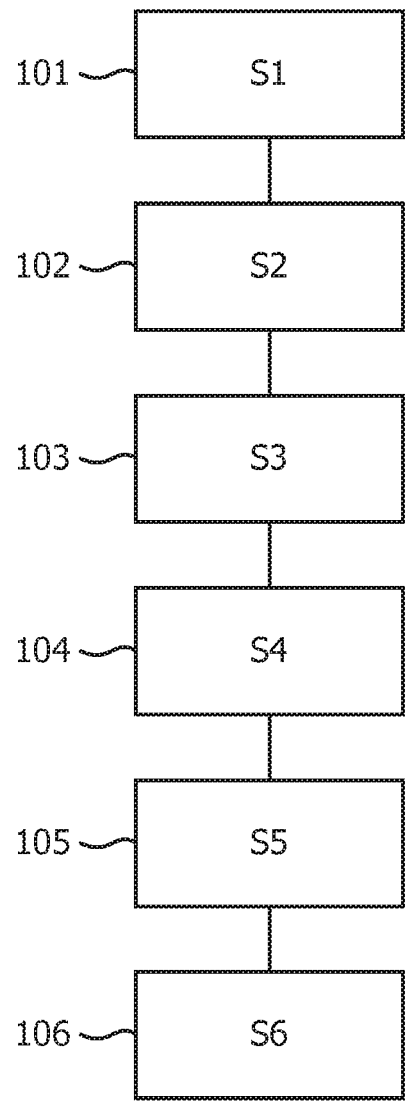
FIG. 8 shows the flowchart of a method for fabricating an ultrasound transducer system according to one aspect of the invention.

FIG. 8 shows the flowchart of a method for fabricating an ultrasound transducer system according to one aspect of the invention.

In step (S1) 101, a flexible foil having openings extending from the top to the bottom surface is provided. The flexible foil may have metallization, e.g. copper) on front and backsides or alternatively has patterned metallization tracks on one of the sides for the front and backside of the piezoelectric material, e.g. PZT. In step (S2) 102, one or more piezoelectric elements is/are mounted into the flexible foil openings. Mounting comprises inserting the one or more piezoelectric elements into the openings of the flexible foil and fastening, e.g. by gluing the one or more piezoelectric elements to the internal rim of the openings of the flexible foil.

In step (S3) 103, one or more conductive layers is/are deposited on the flexible foil and on the one or more piezoelectric elements. Depositing comprises depositing one or more conductive layers on the top and/or bottom surface of the flexible foil and on the top and/or bottom surface of the one or more piezoelectric elements.

In step (S4) 104, the ultrasound transducer assembly produced in the first three steps is positioned onto a base structure which comprises cavities. Positioning the ultrasound transducer assembly on the base structure comprises folding into a 3D structure the flexible foil containing the one or more piezoelectric elements and gluing the folded flexible foil around the base structure.

In step (S5) 105, the cavities of the base structure are filled with backing material. The filling comprises dispensing backing material in a fluidic state and hardening the backing material.

In step (S6) 106, a coating layer is deposited on the external surface of the ultrasound transducer assembly.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An ultrasound transducer assembly comprising:
a base having cavities filled with backing material;
a flexible foil having openings aligned with the cavities, the openings extending from a top surface to a bottom surface of the flexible foil;
one or more piezoelectric elements contained into the openings;
an isolation layer fastening the one or more piezoelectric elements to an internal rim of the openings such that the isolation layer and the one or more piezoelectric elements fully fill the openings;
a first conductive layer deposited on first portions of the flexible foil and on first portions of the one or more piezoelectric elements; and
a second conductive layer located partially on second portions of the flexible foil, second portions of the one or more piezoelectric elements, the isolation layer, the base, and the backing material, the second conductive layer being further located on a side of the backing material between the second portions of the flexible foil and a bottom portion of the backing material,
wherein the isolation layer is confined between the one or more piezoelectric elements and the internal rim of the openings such that top and bottom surfaces of the one or more piezoelectric elements are devoid of the isolation layer for the first and second conductive layers to cover the top and bottom surfaces of the one or more piezoelectric elements and top and bottom surfaces of the isolation layer.

2. An ultrasound transducer system comprising:
an ultrasound transducer assembly placed in a base structure, the base structure having cavities, wherein the cavities are filled with backing material,
the ultrasound transducer assembly comprising:
a flexible foil having openings extending from a top surface to a bottom surface of the flexible foil;
one or more piezoelectric elements contained into the openings;
an isolation layer fastening the one or more piezoelectric elements to an internal rim of the openings such that the isolation layer and the one or more piezoelectric elements fully fill the openings;
a first conductive layer deposited on first portions of the flexible foil and on first portions of the one or more piezoelectric elements; and
a second conductive layer located partially on second portions of the flexible foil, second portions of the one or more piezoelectric elements, the isolation layer, the base and the backing material, the second conductive layer being further located on a side of the backing material between the second portions of the flexible foil and a bottom portion of the backing material,
wherein the isolation layer is confined between the one or more piezoelectric elements and the internal rim of the openings such that top and bottom surfaces of the one or more piezoelectric elements are devoid of the isolation layer for the first and second conductive layers to cover at least one of the top and bottom surfaces of the one or more piezoelectric elements and at least one of top and bottom surfaces of the isolation layer.

3. The ultrasound transducer system according to claim 2, wherein at least one of the cavities extends from a top to a bottom surface of the base structure.

4. The ultrasound transducer assembly according to claim 1, wherein the isolation layer is a layer of glue between at least a side wall of one or more piezoelectric elements and the internal rim of the openings.

5. The ultrasound transducer assembly according to claim 1, wherein flexible the comprises metallization tracks.

6. The ultrasound transducer assembly according to claim 1, further comprising a further isolation layer located over the second conductive layer.

7. A catheter tip comprising an ultrasound transducer assembly according to claim 1.

8. A catheter tip comprising an ultrasound transducer system according to claim 2.

9. A method for fabricating an ultrasound transducer assembly, the method comprising acts of:
   providing a flexible foil having openings extending from a top surface to a bottom surface of the flexible foil;
   mounting one or more piezoelectric elements into the openings using an isolation layer for fastening the one or more piezoelectric elements to an internal rim of the openings, wherein the one or more piezoelectric elements and the isolation layer fully fill the openings;
   depositing a first conductive layer on first portions of the flexible foil and first portions of the one or more piezoelectric elements;
   forming a base having cavities that are aligned with the openings and are filled with backing material; and
   partially depositing a second conductive layer on second portions of the flexible foil, second portions of the one or more piezoelectric elements, the isolation layer, the base and the backing material, the second conductive layer being further located on a side of the backing material between the seoncd portions of the flexible foil and a bottom portion of the backing material,
   wherein the isolation layer is confined between the one or more piezoelectric elements and the internal rim of the openings such that top and bottom surfaces of the one or more piezoelectric elements are devoid of the isolation layer for the first and second conductive layers to cover at least one of the top and bottom surfaces of the one or more piezoelectric elements and at least one of top and bottom surfaces of the isolation layer.

10. The method according to claim 9, wherein the mounting act comprises acts of:
    inserting the one or more piezoelectric elements into the openings; and
    gluing the one or more piezoelectric elements to the internal rim of the openings using the isolation layer.

11. A method for fabricating an ultrasound transducer system, the method comprising acts of:
    fabricating an ultrasound transducer assembly by performing acts of:
       providing a flexible foil having openings extending from a top surface to a bottom surface of the flexible foil;
       mounting one or more piezoelectric elements into the openings using an isolation layer for fastening the one or more piezoelectric elements to an internal rim of the openings, wherein the one or more piezoelectric elements and the isolation layer fully fill the openings;
       depositing a first conductive layer on first portions of the flexible foil and first portions of the one or more piezoelectric elements;
       forming a base having cavities that are aligned with the openings; and
       partially depositing a second conductive layer on second portions of the flexible foil, second portions of the one or more piezoelectric elements, the isolation layer and the base,
    wherein the isolation layer is confined between the one or more piezoelectric elements and the internal rim of the openings such that top and bottom surfaces of the one or more piezoelectric elements are devoid of the isolation layer for the first and second conductive layers to cover at least one of the top and bottom surfaces of the one or more piezoelectric elements and at least one of top and bottom surfaces of the isolation layer;
    positioning the ultrasound transducer assembly onto;
    filling the cavities with backing material, wherein the second conductive layer is further located on a side of the backing material between the second portions of the flexible foil and a bottom portion of the backing material; and
    depositing a coating layer on the external surface of the ultrasound transducer assembly.

12. The method for fabricating an ultrasound transducer system according to claim 11, wherein the positioning act comprises acts of:
    folding into a 3D structure the flexible foil containing the one or more piezoelectric elements; and
    gluing the folded flexible foil around the base.

13. The method for fabricating an ultrasound transducer system according to claim 11, wherein the filling act comprises acts of:
    dispensing the backing material in a fluidic state; and
    hardening the backing material.

* * * * *